(12) United States Patent
Thathagar et al.

(10) Patent No.: US 8,497,384 B2
(45) Date of Patent: Jul. 30, 2013

(54) PROCESS FOR THE PRODUCTION OF CYCLOPROPANE DERIVATIVES

(75) Inventors: Mehul Thathagar, Geleen (NL); Peter Poechlauer, Linz (AT); Sascha Braune, Luftenberg an der Donau (AT)

(73) Assignee: DSM Fine Chemicals Austria NFG GmbH & Co KG, Linz (AT)

( * ) Notice: Subject to any disclaimer, the term of this patent is extended or adjusted under 35 U.S.C. 154(b) by 182 days.

(21) Appl. No.: 13/129,213

(22) PCT Filed: Nov. 12, 2009

(86) PCT No.: PCT/EP2009/065075
§ 371 (c)(1),
(2), (4) Date: Jul. 27, 2011

(87) PCT Pub. No.: WO2010/055106
PCT Pub. Date: May 20, 2010

(65) Prior Publication Data
US 2011/0301359 A1    Dec. 8, 2011

(30) Foreign Application Priority Data

Nov. 14, 2008    (EP) .................................. 08169209

(51) Int. Cl.
*C07D 333/78*    (2006.01)

(52) U.S. Cl.
USPC .......................................... 549/52

(58) Field of Classification Search
USPC .......................................... 549/52
See application file for complete search history.

(56) References Cited

FOREIGN PATENT DOCUMENTS

EP    0 774 461    5/1997
WO    2004/016348    2/2004

OTHER PUBLICATIONS

International Search Report for PCT/EP2009/065075, dated Mar. 16, 2010.
Written Opinion for PCT/EP2009/065075, mailed Mar. 16, 2010.

Diaz-Requejo et al.: "Copper, silver and gold-based catalysts for carbene addition or insertion reactions" Journal of Organometallic Chemistry, Elsevier-Sequioa S.A. Lausanne, CH, vol. 690, No. 24-25, Dec. 1, 2005, pp. 5441-5450, XP005391742.
C. Wiles et al.: "Continuous Flow Reactors, a Tool for the Modern Synthetic Chemist" Eur J Org Chem., Jan. 29, 2008, pp. 1655-1671, XP002526283.

*Primary Examiner* — Taofiq A Solola
(74) *Attorney, Agent, or Firm* — Nixon & Vanderhye P.C.

(57) ABSTRACT

A process for the preparation of a cyclopropane derivative of Formula (I), by reacting an olefin of Formula (II), with a carbene of the formula:$CR^1R^2$, in a reaction vessel, optionally in the presence of a solvent, wherein $R^1$ and $R^2$ are each independently hydrogen, $C_1$-$C_6$ alkyl, $C_2$-$C_6$ alkenyl, aryl, heteroaryl, heterocyclyl, carbocyclyl, heterocyclyl, —C(O)$R^7$ or —$NR^8_2$; $R^3$, $R^4$, $R^5$ and $R^6$ are each independently hydrogen, $C_1$-$C_6$ alkyl, $C_1$-$C_6$ alkoxy, $C_2$-$C_6$ alkenyl, aryl, aryloxy, heteroaryl, heterocyclyl, carbocyclyl, heterocyclyl, —C(O)$R^9$, —$NR^{10}_2$, —$SR^{11}$, —S(O)$R^{11}$, or —$SO_2R^{11}$, or $R^3$ and $R^6$ are as defined above and $R^4$ and $R^5$ together form a ring, which ring is carbocyclyl, heterocyclyl, aromatic or heteroaromatic; $R^7$ is hydrogen, hydroxy, $C_1$-$C_6$ alkyl, $C_1$-$C_6$ alkoxy, aryl, aryloxy, heteroaryl or —$NR^{10}_2$; $R^8$ is hydrogen, $C_1$-$C_6$ alkyl, $C_1$-$C_6$ alkenyl, aryl, heteroaryl, carbocyclyl or heterocyclyl; $R^9$ is hydrogen, hydroxy, $C_1$-$C_6$ alkyl, $C_1$-$C_6$ alkoxy, aryl, aryloxy or heteroaryl; $R^{10}$ is hydrogen, $C_1$-$C_6$ alkyl, $C_2$-$C_6$ alkenyl, aryl, heteroaryl, carbocyclyl, heterocyclyl or C(O)$R^{12}$; $R^{11}$ is hydrogen, $C_1$-$C_6$ alkyl, $C_2$-$C_6$ alkenyl, aryl, heteroaryl, carbocyclyl or heterocyclyl; and $R^{12}$ is hydrogen, hydroxy, $C_1$-$C_6$ alkyl, $C_1$-$C_6$ alkoxy, aryl, or aryloxy, in the presence of copper metal or copper oxide, wherein the process is a continuous process.

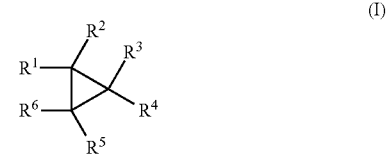

(I)

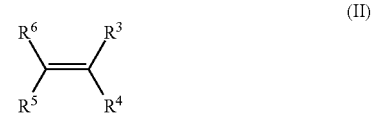

(II)

15 Claims, No Drawings

PROCESS FOR THE PRODUCTION OF CYCLOPROPANE DERIVATIVES

This application is the U.S. national phase of International Application No. PCT/EP/2009/065075 filed 12 Nov. 2009 which designated the U.S. and claims priority to EP Patent Application No. 08169209.7 filed 14 Nov. 2008, the entire contents of each of which are hereby incorporated by reference.

The present invention concerns a process for preparing a cyclopropane derivative through addition of a carbene to an olefin, using copper metal or copper oxide as a catalyst.

Cyclopropane derivatives are useful intermediates in the production of pharmaceutically active compounds. They are commonly made through the addition of a carbene moiety to an olefin in the presence of a transition metal complex catalyst, such as a rhodium or palladium complex. Due to the high costs of metals such as rhodium and palladium, an alternative process avoiding the use of such catalysts is desirable.

Further, carrying out a carbene addition reaction using a metal complex catalyst requires a step of separating the catalyst from the product, so that the catalyst may be reused. It is desirable to find a catalyst which does not require a separation step, so that the reaction may be achieved simply and therefore at low cost. This would enable an efficient continuous process for the production of the desired cyclopropane derivative to be used.

The catalytic addition of carbenes to olefins is well documented in the prior art, for example by Doyle in Chem. Rev. (1986) 86, 919-39. Copper, silver and gold-complex catalysts are discussed by Diaz-Requejo and Perez in J. Organometallic Chemistry (2005) 690, 5441-50. The use of rhodium and copper catalysts in cyclopropanation are mentioned in EP0774461A1. Further copper complex catalysts are described in JACS (1973) 95:10, 3300-3310.

Carbenes may be generated by the elimination of $N_2$ from diazo compounds. The synthesis of diazo compounds is well established, for example diazomethane may be produced from N-methyl-N-nitroso-p-toluene sulfonamide, and diazo acetates may be produced by nitrosation of glycine ester. Reactions of diazo compounds are described in the following references: Brückner, Reaktionsmechanismen, 3 Auflage (2004), Spectrum Akad. Verlag. ISBN 3-8274-1579-9; Greiss, Annalen der Chemie, 1858, 106, 123; and Bollinger, Tuma, L. D. Synlett (1996) 407. However, diazo compounds are potentially dangerous compounds; the elimination of $N_2$ causes rapid reaction, which may generate large amounts of heat and potential explosion, so great care must be taken in their use.

The use of continuous flow reactors is described by Wiles and Watts in Eur. J. Org. Chem. (2008) 10, 1655-71.

There remains a need for a synthesis of cyclopropane derivatives, which is economical and practical on an industrial scale. A further need is for the synthesis of cyclopropanes from readily available starting materials by a method which is not only economical and practical but also safe and reliable. Still further, there is an object to reduce the impact on the environment by production of cyclopropane derivatives on an industrial scale by minimising the generation of waste products, or energy used to treat waste products.

The present inventors have surprisingly found that copper metal and copper oxide have a catalytic effect in the addition of certain carbenes to olefins. The degree of catalysis has been found to enable an economically favourable process compared with the use of known rhodium metal complex catalysts.

Accordingly, the present invention provides a process for the preparation of a cyclopropane derivative of Formula (I),

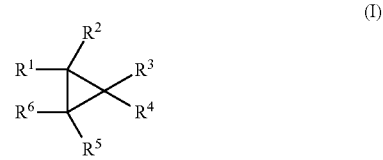

by reacting an olefin of Formula (II),

with a carbene of the formula: $CR^1R^2$, in a reaction vessel, optionally in the presence of a solvent, wherein, $R^1$ and $R^2$ are each independently hydrogen, $C_1$-$C_6$ alkyl, $C_2$-$C_6$ alkenyl, aryl, heteroaryl, heterocyclyl, carbocyclyl, heterocyclyl, —C(O)$R^7$ or —$NR^8{}_2$;

$R^3$, $R^4$, $R^5$ and $R^6$ are each independently hydrogen, $C_1$-$C_6$ alkyl, $C_1$-$C_6$ alkoxy, $C_2$-$C_6$ alkenyl, aryl, aryloxy, heteroaryl, heterocyclyl, carbocyclyl, heterocyclyl, —C(O)$R^9$, —$NR^{10}{}_2$, —$SR^{11}$, —S(O)$R^{11}$, or —$SO_2R^{11}$, or $R^3$ and $R^6$ are as defined above and $R^4$ and $R^5$ together form a ring, which ring is carbocyclyl, heterocyclyl, aromatic or heteroaromatic;

$R^7$ is hydrogen, hydroxy, $C_1$-$C_6$ alkyl, $C_1$-$C_6$ alkoxy, aryl, aryloxy, heteroaryl or —$NR^{10}{}_2$;

$R^8$ is hydrogen, $C_1$-$C_6$ alkyl, $C_1$-$C_6$ alkenyl, aryl, heteroaryl, carbocyclyl or heterocyclyl;

$R^9$ is hydrogen, hydroxy, $C_1$-$C_6$ alkyl, $C_1$-$C_6$ alkoxy, aryl, aryloxy or heteroaryl;

$R^{10}$ is hydrogen, $C_1$-$C_6$ alkyl, $C_2$-$C_6$ alkenyl, aryl, heteroaryl, carbocyclyl, heterocyclyl or C(O)$R^{12}$;

$R^{11}$ is hydrogen, $C_1$-$C_6$ alkyl, $C_2$-$C_6$ alkenyl, aryl, heteroaryl, carbocyclyl or heterocyclyl; and $R^{12}$ is hydrogen, hydroxy, $C_1$-$C_6$ alkyl, $C_1$-$C_6$ alkoxy, aryl, or aryloxy, in the presence of copper metal or copper oxide, wherein the process is a continuous process.

As used herein $C_1$-$C_6$ alkyl means an alkyl group comprising from 1 to 6 carbon atoms. It may be branched or unbranched. Typically it is a $C_1$-$C_4$ alkyl group, preferably a $C_1$-$C_2$ alkyl group. Examples include methyl ethyl, $^n$propyl, $^i$propyl, $^n$butyl, $^s$butyl and $^t$butyl. Unless otherwise specified, an alkyl group may be substituted or unsubstituted.

As used herein $C_2$-$C_6$ alkenyl means an alkyl group comprising from 2 to 6 carbon atoms and at least one C=C bond. It may be branched or unbranched. Typically it is a $C_2$-$C_4$ alkenyl group. Examples include ethenyl, propenyl and butenyl. If an alkenyl group contains more than one C=C bond, preferably they are conjugated. Unless otherwise specified, an alkenyl group may be substituted or unsubstituted, but is preferably unsubstituted.

As used herein $C_1$-$C_6$ alkoxy means a $C_1$-$C_6$ alkyl group as defined above bonded through an oxygen atom. Similarly a $C_1$-$C_4$ alkoxy group is a $C_1$-$C_4$ alkyl group as defined above bonded through an oxygen atom.

As used herein aryl means a mono-, bi- or tricyclic aromatic hydrocarbon ring system. Aryl includes fused ring systems in which an aryl group is fused to a monocyclic carbocyclyl or heterocyclyl group. Examples of aryl groups include phenyl, naphthyl and anthracyl groups. Phenyl is preferred. Unless otherwise specified, an aryl group may be substituted or unsubstituted.

As used herein aryloxy means an aryl group as defined above bonded through an oxygen atom.

As used herein heteroaryl means a mono-, bi- or tricyclic aromatic ring system wherein at least one ring contains at least one heteroatom selected from O, N and S. Heteroaryl includes fused ring systems in which a heteroaryl group is fused to a monocyclic carbocyclyl or heterocyclyl group. Typically it contains one or two heteroatoms, preferably one, in any one aromatic ring. Preferably it is a monocyclic system. Examples include pyridyl, pyrazinyl, pyridazinyl, pyrimidinyl, pyrrolyl, furanyl, thienyl, imidazolyl, pyrazolyl, oxazolyl, isoxazolyl, thiazolyl and isothiazolyl. Particularly preferred are thienyl and furanyl, more preferably thienyl. Unless otherwise specified, a heteroaryl group may be substituted or unsubstituted, but is preferably unsubstituted.

As used herein a carbocyclyl group is a non-aromatic saturated or unsaturated hydrocarbon ring. Typically it has from 3 to 7 carbon atoms. Preferably it is a saturated hydrocarbon ring (i.e. a cycloalkyl group). Preferably it has 5 or 6 carbon atoms. Examples include cyclopropyl, cyclobutyl, cyclopentyl and cyclohexyl. Unless otherwise specified, a carbocyclyl group may be substituted or unsubstituted, but is preferably unsubstituted.

As used herein heterocyclyl means a non-aromatic, monocyclic saturated or unsaturated carbocyclic ring, typically having from 5 to 10 carbon atoms, in which one or more, for example 1, 2 or 3, of the carbon atoms is replaced by a heteroatom selected from N, O and S. Saturated heterocyclyl groups are preferred. Examples include tetrahydrofuranyl, tetrahydrothienyl, pyrrolidinyl, imidazolidinyl, pyrazolidinyl, dioxolanyl, thiazolidinyl, tetrahydropyranyl, piperidinyl, dioxanyl, piperazinyl, morpholinyl, thiomorpholinyl and thioxanyl. Unless otherwise specified, a heterocyclyl group may be substituted or unsubstituted, but is preferably unsubstituted.

As used herein halogen means fluorine, chlorine, bromine or iodine. Preferably it is fluorine or chlorine, more preferably chlorine.

A group is substituted when one or more hydrogen atoms on the group is replaced by a different moiety. Where substituted, typically a group bears one or two substituents, preferably one. A substituent may not itself be further substituted. Typical substituents are halogen, $C_1$-$C_6$ alkyl, $C_2$-$C_6$ alkenyl, $C_1$-$C_6$ alkoxy, aryl, aryloxy, heteroaryl, carbocyclyl, heterocyclyl, —C(O)$R^{13}$ or —N$R^{14}_2$, wherein, $R^{13}$ is hydrogen, hydroxy, $C_1$-$C_6$ alkyl, $C_1$-$C_6$ alkoxy, aryl, or aryloxy; and each $R^{14}$ is independently hydrogen, $C_1$-$C_6$ alkyl, aryl, heteroaryl, carbocyclyl or heterocyclyl.

A solvent is selected from those suitable for dissolving the diazo compound and the olefin. The solvent should be inert under the reaction conditions. Accordingly, saturated solvents are preferred. Particularly preferred solvents include dichloroethane and dichloromethane. The solvent may also be a mixture of solvents. For given substrates (diazo compound and olefin) the skilled person can determine an appropriate solvent by routinely testing their solubility and inertness to reaction in a proposed solvent. Preferably, however, no solvent is present.

As used herein copper metal means solid metal comprising at least 90% by weight Cu(0) atoms. The Cu(0) atoms may be defined as elemental copper. Preferably the metal comprises at least 95% by weight Cu(0) atoms. More preferably it comprises at least 97%, at least 98%, at least 99% or most preferably at least 99.5% by weight Cu(0) atoms. Preferably the metal is pure, or at least substantially pure, copper metal. Because the copper metal has a catalytic effect, no further catalyst is required in the above-described reaction. Typically a catalyst other than the above described copper metal is not used in the process of the present invention.

The copper metal may be in any suitable form, for example particles of copper metal, a coating of copper metal on substrate particles, a coating of copper metal on the inside of the reaction vessel, or the reaction vessel itself. The aforementioned coatings may be in the form of nanoparticles.

The copper metal may be applied by techniques known in the art. Where the inside of the reaction vessel is coated with copper metal, for example, molten copper metal may be poured through the reaction vessel. Where the copper metal is present on substrate particles, the copper metal may be applied by depositing a copper salt, for example $CuCl_2$ on the substrate surface and reducing it using, for example $NaBH_4$, or hydrogen at high temperature.

As used herein copper oxide means solid CuO or $Cu_2O$. Preferably copper oxide is CuO. The copper oxide may be in any suitable form, for example particles of copper oxide, a coating of copper oxide on substrate particles or a coating of copper oxide on the inside of the reaction vessel.

The copper oxide may be applied by techniques known in the art. For example, since copper metal can be easily oxidised in the presence of oxygen in air or some other oxidation agent, copper oxide may be produced simply by flowing an oxygen containing gas over a copper metal surface. One example is to flow air through a copper (or copper coated) reaction vessel. A further example is to electrodeposit a thin film of $Cu_2O$ onto copper metal by reduction of copper lactate.

Where particles of copper metal or copper oxide, or a coating of copper metal or copper oxide on substrate particles, are used, said particles may be held in place inside the reaction vessel by supporting structure, for example a fine-mesh cage. One advantage of using particles within a supporting structure is that the pressure drop across the reactor is raised. This leads to increased turbulence in the flow of the reaction mixture passing through the reactor and better mixing of the reagents. By continuous process, it is meant a process in which the starting material may be continuously added to a reaction vessel and the product continuously withdrawn from the reaction vessel. The rate of addition and removal of materials maintains the reaction volume at a specific level. In other words a continuous reaction is one wherein a steady state of reaction volume is achieved. For instance, the olefin of Formula (II) may be continuously added, and the cyclopropane derivative of Formula (I) continuously withdrawn, from the reaction vessel. A continuous process is therefore distinct from a batch process. A continuous process involves the input of one or more feed streams into the reaction vessel, and the withdrawal of a product stream from the reaction vessel. The product stream contains at least the desired product, for example, the cyclopropane derivative of Formula (I).

By reaction vessel, it is meant either a distinct apparatus or a portion of an apparatus within which the defined reaction occurs.

The carbene of formula:$CR^1R^2$ is preferably generated in situ from a diazo compound of the formula $N_2CR^1R^2$ wherein $R^1$ and $R^2$ areas defined above. In this process $N_2$ is generated. By generated in situ it is meant generated in the reaction vessel in which the carbene addition to the olefin occurs. The starting material for this process is the diazo compound, while the reactive species is the carbene compound.

Methods for the synthesis of the diazo compound of formula $N_2CR^1R^2$ and the olefin of Formula (II) are taught in the prior art, either directly or by analogy with a directly described synthesis.

Typically $R^1$ and $R^2$ are each independently hydrogen, $C_1$-$C_6$ alkyl, —C(O)$R^7$ or —$NR^8_2$. Preferably $R^1$ and $R^2$ are each independently hydrogen, —C(O)$R^7$ or —$NR^8_2$. More preferably $R^1$ and $R^2$ are each independently hydrogen, —C(O)$R^7$, or —$NR^8_2$, wherein $R^7$ is hydroxy or $C_1$-$C_6$ alkoxy (preferably methyl or ethyl), and each $R^8$ is hydrogen. When one of $R^1$ and $R^2$ is —$NR^8$, preferably the other of $R^1$ and $R^2$ is hydrogen. Particularly preferred are the combinations: $R^1$ and $R^2$ are each —$CO_2Me$; $R^1$ and $R^2$ are each —$CO_2Et$; $R^1$ is —$CO_2Me$ and $R_2$ is H; $R^1$ is —$CO_2Me$ and $R^2$ is H; and $R^1$ is —$NH_2$ and $R^2$ is H.

Typically $R^3$, $R^4$, $R^5$ and $R^6$ are each independently hydrogen, $C_1$-$C_6$ alkyl, $C_2$-$C_6$ alkenyl, aryl, heteroaryl, heterocyclyl, carbocyclyl or heterocyclyl, or $R^3$ and $R^6$ are as defined above and $R^4$ and $R^5$ together form a ring, which ring is carbocyclyl, heterocyclyl, aromatic or heteroaromatic. Preferably $R^4$ and $R^5$ together form a ring.

When $R^4$ and $R^5$ form a ring, preferably the ring is aromatic or heteroaromatic. More preferably it is heteroaromatic; for example furan or thiophene; most preferably thiophene. Preferably, when $R^4$ and $R^5$ form a ring, $R^3$ and $R^6$ are each hydrogen or $C_1$-$C_6$ alkyl, most preferably hydrogen. Most preferably the olefin of Formula (II) is thiophene.

When $R^4$ and $R^5$ do not form a ring, typically $R^3$, $R^4$, $R^5$ and $R^6$ are each independently hydrogen, $C_1$-$C_6$ alkyl, $C_2$-$C_6$ alkenyl, aryl or heteroaryl. Preferably $R^3$, $R^4$, $R^5$ and $R^6$ are each hydrogen, $C_2$-$C_6$ alkenyl or aryl. More preferably, $R^3$ is hydrogen, $C_2$-$C_6$ alkenyl or aryl, and each of $R^4$, $R^5$ and $R^6$ are hydrogen. Still more preferably, $R^3$ is hydrogen, ethenyl or phenyl, and each of $R^4$, $R^5$ and $R^6$ are hydrogen.

$R^7$ is typically hydroxy, $C_1$-$C_6$ alkoxy, or aryloxy. Preferably $R^7$ is hydroxy or $C_1$-$C_6$ alkoxy. More preferably $R^7$ is hydroxy, methoxy or ethoxy.

Each $R^8$ is typically hydrogen or $C_1$-$C_6$ alkyl. Preferably at least one $R^8$ on a given nitrogen atom is hydrogen. More preferably both $R^8$ on a given nitrogen atom are hydrogen.

$R^9$ is typically hydroxy, $C_1$-$C_6$ alkoxy, or aryloxy. Preferably $R^9$ is hydroxy or $C_1$-$C_6$ alkoxy. More preferably $R^9$ is hydroxy, methoxy or ethoxy.

Each $R^{10}$ is typically hydrogen or $C_1$-$C_6$ alkyl. Preferably at least one $R^{10}$ on a given nitrogen atom is hydrogen. More preferably both $R^{10}$ on a given nitrogen atom are hydrogen.

$R^{11}$ is typically hydrogen, $C_1$-$C_6$ alkyl, or aryl. Preferably $R^{11}$ is hydrogen $C_1$-$C_6$ alkyl, for example methyl or ethyl, or phenyl.

$R^{12}$ is typically hydroxy, $C_1$-$C_6$ alkoxy or aryloxy. Preferably $R^{12}$ is hydroxy or $C_1$-$C_6$ alkoxy, for example methoxy or ethoxy.

In one embodiment of the present invention, in order to simplify the present process further and therefore reduce the cost of the process, the copper metal described above may form part of the reaction vessel. This avoids the need for a separate catalyst material to be added to the reaction vessel and be separated from the product stream. Accordingly, the process of the present invention is typically carried out in a reaction vessel, wherein a portion of the inner surface of the reaction vessel is copper metal. Preferably the inner surface of said reaction vessel is substantially, preferably completely, copper metal. More preferably said reaction vessel is itself copper metal. In its simplest form the reaction vessel may be a copper tube.

By a portion of the inner surface of the reaction vessel is meant any amount. However, a preferred amount may be defined by the surface area to volume ratio of the copper surface area to volume of the reaction mixture in the reaction vessel. In a tube of D mm inner diameter this is $(D\pi)/[(D/2)^2\pi]$ mm$^2$/mm$^3$. For example, in a tube of 1 mm inner diameter the ratio is 4 mm$^2$/mm$^3$, or 4000 m$^2$/m$^3$. Typically the copper surface area per volume of reaction mixture in the reaction vessel is at least 500 m$^2$/m$^3$. Preferably, it is at least 1000 m$^2$/m$^3$. In embodiments of the invention where the copper metal is not necessarily part of the inner surface of the reaction vessel, the copper surface area per volume of reaction mixture in the reaction vessel is also typically at least 500 m$^2$/m$^3$, preferably, at least 1000 m$^2$/m$^3$.

As mentioned above, the elimination of $N_2$ from a diazo compound to yield a carbene may generate large amounts of heat and potential explosion. Carbenes themselves are also highly reactive, releasing their reaction energy quickly and causing a rapid increase in temperature of the reaction mixture. There is a potential for such a reaction to become "runaway", or to lose selectivity of product, unless controlled, for example by low temperature or low dilution of the carbene. Accordingly, great care must be taken in handling reaction of diazo compounds. In a preferred process of the present invention, the diazo compound is converted to a carbene which is then, without isolation, added to an olefin to produce a cyclopropane derivative. The reaction of the present invention is therefore preferably carried out in conditions and using equipment which minimize the risk of reaction "runaway" explosion. Typically, the reaction of the present invention is carried out in a reaction vessel, wherein the reaction vessel is a microreactor.

As used herein, a microreactor means a micro- or minireactor. Each of these differ only from conventional size reactors in the dimensions and constructions of the reaction channel structures.

As used herein a microreactor is a miniaturized reactor with characteristic dimensions (channel width and depth, or plate width) in micrometers to millimeters. The characteristic dimensions are the dimensions perpendicular to the flow of the reaction mixture through the microreactor. Typically the characteristic dimensions are 20 mm or less. Preferably, the characteristic dimensions are from 0.01 mm to 10 mm; more preferably from 0.5 to 2 mm.

A number of microreactors may be combined in parallel to form a micro-structured reactor. Thus, the volume available for reaction depends on the diameter and length of the microreactor and, in the case a micro-structured reactor is used, on the dimension of the parallel channels and the number of parallel channels. The total volume of a micro-reactor or micro-structured reactor typically lies in the range of from 1 ml to 1 m$^3$, preferably from 10 ml to 50 liters.

Preferably, a microreactor is defined as a reactor having a channel with a hydraulic diameter of 20 mm or less. The hydraulic diameter $D_h$ is defined as 4A/U, wherein A is the cross sectional area of the reactor channel and U is the perimeter of said cross section. More preferably the hydraulic diameter is from 0.01 mm to 10 mm, still more preferably from 0.5 to 2 mm.

For a round tube, the hydraulic diameter $D_h$ equals the diameter of the tube. For a rectangular duct, that has a cross section with a rectangular shape, the hydraulic diameter equals 4LW/2(L+W), wherein L is the length of the longest side of the rectangle and W is the width of the rectangle. For the special case of a square duct, the hydraulic diameter $D_h$ equals L. For an annulus, the hydraulic diameter is $D_h = (4 \cdot 0.25\pi(D_o^2 - D_i^2))/\pi(D_o - D_i) = D_o - D_i$, wherein $D_o$ is the outer diameter of the annulus and $D_i$ is the inner diameter. However, it should be noted that the general formula 4A/U, wherein A is the cross sectional area of the reactor channel and U is the perimeter of said cross section, allows calculation of the hydraulic diameter for any shape of reactor channel.

The microreactor used in the process of the present invention, is suitable for continuous processes. The reaction set-up to be used in the process according to the invention comprises a miniaturized reactor with discrete flow passages for receiving feed streams and for emitting a product stream.

The microreactor consists of a device allowing the reactants to enter and continuously flow through. The reactants are contacted with each other in the device, allowing a chemical reaction to take place in a narrow confined space like a channel or between two plates. One (in the case of plates) or two (in case of channels or grooves) dimensions of the micro reactor are chosen in such a way that the characteristic times for heat transfer and/or mass transfer are very low. Therefore high rates of reaction and heat transfer can be handled in a controlled fashion. The heat is transferred to or from a heat transfer fluid that does not come into contact with the reactants or the products.

A number of microreactors may be combined in parallel to form a micro structured reactor. Entering reactants are distributed over manifold systems or other distribution systems to the individual microreactors. Each micro-structured reactor may include mixing zones to mix the entering reactants and/or the reaction medium. Each micro-structured reactor may contain residence zones to allow the reaction medium to obtain sufficient conversion. The micro-structured reactor may be constructed of, or may contain, a number of parallel sub-units (mixing zones with residence zones) in a numbering-up concept to obtain sufficient production capacity. An example is a multi channel monolith reactor for example.

Microreactors, micromixers, micro-heat-exchangers have been developed, for example in Germany (i.e.: IMM, Mainz, and Forschungszentrum Karlsruhe) and in the USA (i.e.: MIT and DuPont).

The process of the present invention is preferably performed in multi channel micro structured reactor, such as for example a monolith reactor, a HEX reactor or a printed circuit heat exchange reactor. The channel hydraulic diameter is preferably from 0.01 to 10 mm, more preferably from 0.1 to 1 mm. The liquid flow may be a one phase or a multi phase system. The length of the channels depends on the desired residence time, which may vary for example from 0.01 sec to 1000 sec, and is preferably from 1 sec to 100 sec.

Preferably the inner surface of the micro reactor is substantially, preferably completely, copper metal. More preferably the microreactor itself is copper metal.

A microreactor provides high mass transfer and high heat transfer capacity to the reaction. By carrying out the process in a microreactor, safety concerns are reduced and the existence of hazardous conditions minimized. The danger of explosion is eliminated or at least the risks of explosions are drastically reduced. In fact, one advantage of using a microreactor is that it permits harsher conditions to be used, for example higher temperatures and higher concentration of reagents. This increases the yield of the reaction and makes the use of less efficient catalysts economically more feasible than, for example, the previously known more efficient rhodium complex catalysts.

An advantage of the microreactor being made of copper is the cost of manufacture of the microreactor. Such a device is more simple, being made entirely of one material. Further, copper is a material which is easy to machine and easy to chemically etch, and therefore the device may be manufactured easily and at relatively low cost. It is itself a low cost raw material.

Carbenes are highly reactive species, practically all having lifetimes of under 1 second. Reaction of a carbene with an olefin to form a cyclopropane derivative occurs in competition with dimerisation of the carbene, an undesirable side reaction. To reduce the chance of carbene dimerisation, conventionally the reaction is carried out with a low concentration of the diazo compound from which the carbene is generated. A typical concentration of the diazo compound in a solvent is from 0.5 to 5 wt %, preferably 1 to 2 wt %. Accordingly a high volume of solvent would be required to carry out the reaction. In the present process, in order to prevent waste, where a solvent is present, it is therefore preferred to recycle the solvent. By this it is meant separating a portion of the solvent from the product stream, adding diazo compound to the separated solvent and feeding the diazo compound in solvent into the reaction vessel, in a feed stream. Solvent is typically separated from product by distillation by methods known in the art.

A suitable solvent is one which does not interfere with the cyclopropanation reaction of the present invention, for example a saturated solvent. Preferred solvents can be selected by the skilled person Further, to increase the rate of addition to the olefin to produce a cyclopropane derivative, a high molar proportion of olefin compared with the diazo compound is preferred. Accordingly, the product stream would contain unreacted olefin. In order to prevent waste, for the same reasons as the recycling of solvent, it is therefore preferred to recycle the unreacted olefin. By this it is meant separating the unreacted olefin from the product stream and feeding the unreacted olefin back into the reaction vessel. The olefin is typically separated from the product by distillation by methods known in the art.

Preferably the diazo compound is soluble in the olefin. In this case, there is no need for a solvent in the reaction. The skilled person can determine by routine experiment whether a given diazo compound is soluble in a given olefin. An example is ethyldiazo acetate dissolving in thiophene. An advantage of such a process is that no other solvent is required. Therefore there will be little or preferably no wasted solvent or olefin of Formula (II), because it can be recycled and, as a reagent, reacted with carbene. In other words, preferably no solvent is present.

As discussed above, the diazo compound of the formula $N_2CR^1R^2$ may be made by methods known in the art. One hazard associated with the use of diazo compounds in general is that they have a potential to decompose, by elimination of $N_2$, in a highly exothermic and explosive reaction. It is therefore desirable to minimize the storage and transportation of diazo compounds. One method of doing this is by preparing the diazo compound immediately before it is required. In one embodiment of the present invention the diazo compound is itself produced in a continuous process. Preferably the process of the present invention comprises the steps of producing the diazo compound of the formula $N_2CR^1R^2$ in a continuous process and continuously with the preparation of the cyclopropane of Formula (I). In other words there is a continuous process from the starting materials for the diazo compound to the cyclopropane derivative of Formula (I). This process involves producing a diazo compound and reacting the diazo compound via a carbene with an olefin to yield a cyclopropane derivative.

The formation of diazo compound will typically involve several steps. A preferred diazo compound is ethylenediazoacetate ($N_2CHCO_2Et$). Its preparation typically involves i) dissolving glycine ester salt in water with thiophene; ii) addition of $NaNO_2$ in water, followed by iii) addition of sulphuric acid to effect diazo transfer. These three steps may be carried out continuously. The produced ethylenediazoacetate may then be provided continuously as a feed stream to the reaction vessel for the continuous reaction with the olefin of Formula (II).

The advantages of using a completely continuous reaction are the ease of use, the overall efficiency of the process and the fact that storage and transportation of potentially explosive materials is avoided.

A further difficulty of using diazo compounds is that the reactions used for their formation typically involve a highly exothermic step, for instance diazo transfer, which reactions should in conventional reaction vessels therefore be carried out at low temperature. For example the synthesis of ethylenediazoacetate by diazo transfer is conventionally carried out at −23° C. If the diazo transfer of this reaction is carried out in an environment which can operate at a higher temperature by rapid heat transfer, the rate of reaction can be increased in a controlled and safe manner.

An environment which can rapidly dissipate the heat generated can be provided by a microreactor. Therefore, preferably the diazo compound of formula $N_2CR^1R^2$ is produced by a process utilizing at least one microreactor. Preferably, the diazo compound of formula $N_2CR^1R^2$ is produced by a process involving diazo transfer. If the diazo compound of formula $N_2CR^1R^2$ is produced by a process involving diazo transfer, preferably at least this step is carried out in a microreactor. More preferably all steps in the synthesis of the diazo compound are carried out in a microreactor, or series of microreactors.

The microreactor suitable for use in producing the diazo compound is as described above, except that there is no requirement for it to comprise copper metal.

The present invention may therefore be carried out in a series of two or more microreactors. It will be understood that the reaction system could alternatively comprise two or more continuous micro-structured reactors, rather than two or more continuous microreactors.

In one embodiment, all steps of the process of the present invention are carried out in a sequence of microreactors so that the process can be performed in a safe way with low hold-up of the reactive or hazardous intermediates. A further advantage of such a process is the increased productivity or yield as a result of the direct conversion of unstable intermediates.

Typically, in the process of the present invention, the addition of carbene to olefin is carried out at a temperature of from 50 to 300° C., preferably 100 to 200° C.

Typically, in the process of the present invention, the addition of carbene to olefin is carried out at a pressure from atmospheric to 150 bar, preferably 100 bar.

Typically, in the process of the present invention, the addition reaction of carbene to olefin is carried out with a residence time of from 0.5 seconds to 20 minutes, preferably 1 second to 10 minutes, more preferably 5 seconds to 5 minutes, yet more preferably from 10 seconds to 3 minutes. Residence time is the average time taken for the reaction mixture to spend in the reaction vessel. Since, in a continuous process, the reaction mixture flows through the reaction vessel, this can be measured as the time taken for the reaction mixture to pass through the reaction vessel.

Typically, in the process of the present invention, the addition reaction of carbene to olefin is carried out with a concentration of from 0.5 to 5 wt %, preferably 1 to 2 wt % of diazo compound in the solvent. The concentration of olefin is typically higher than that of the diazo compound, for example typically 0.5 to 5 wt %, preferably 1 to 2 wt %. Preferably the olefin is used neat. The relative concentrations of the olefin to diazo compound will be determined by the amount of each component supplied to the reactor in the feed streams. Typically the molar ratio of olefin of Formula (II) to diazo compound of formula $N_2CR^1R^2$ is from 1 to 20, preferably 2 to 10, more preferably 3 to 5.

A preferred embodiment of the present invention is a process as described above, wherein the cyclopropane derivative of Formula (I) is a cyclopropane derivative of Formula (I'),

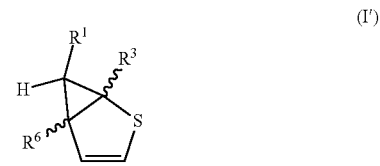

wherein $R^1$, $R^3$ and $R^6$ are as described above.

A particularly preferred embodiment of the invention is a process as described above, wherein the cyclopropane derivative of Formula (I) is a cyclopropane derivative of Formula (Ia),

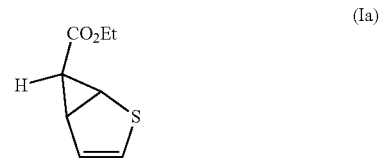

the olefin of Formula (II) is thiophene, the carbene of formula: $CR^1R^2$ is ethoxycarbonyl carbene (:CHCO$_2$Et) and the diazo compound of formula $N_2CR^1R^2$ is ethyldiazoacetate ($N_2$CHCO$_2$Et).

The cyclopropane derivative of Formula (Ia) has the steroismers (Ib) to (Ie),

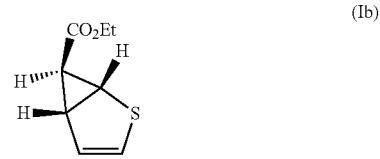 [SMILES: CCOC(=O)[C@@H]1[C@H]2C=CS[C@H]21]

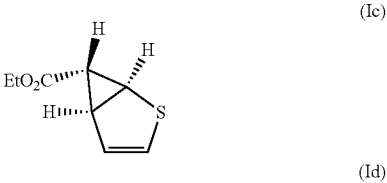

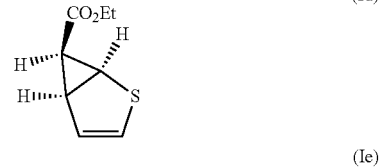

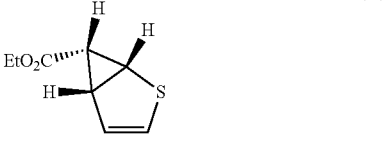

The major steroisomers of the cyclopropane derivative of Formula (Ia) produced by the process of the invention are (Ib) and (Ic). The compound (Ib) is particularly preferred. The cyclopropane derivative of Formula (Ib) or (Ic) may be isolated from the other produced stereoisomers of (Ia). Isolation may be carried out by conventional techniques. A preferred embodiment of the present invention is a process as defined above, further comprising the step of isolating a cyclopropane derivative of (Ib),

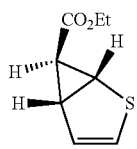
(Ib)

from the cyclopropane derivative of Formula (Ia).

A preferred embodiment of the present invention is a process for the preparation of a cyclopropane derivative of Formula (Ia),

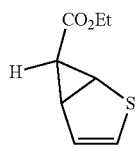
(Ia)

by reaction of thiophene with:CHCO$_2$Et, generated in situ from ethyldiazoacetate (N$_2$CHCO$_2$Et), in a copper metal microreactor, wherein the thiophene acts as a solvent and is recycled; the ethyldiazoacetate is produced in a continuous process, utilizing at least one microreactor, and continuously with the preparation of the cyclopropane derivative of Formula (Ia). Preferably the process further comprising the step of isolating a cyclopropane derivative of (Ib),

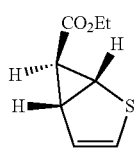
(Ib)

from the cyclopropane derivative of Formula (Ia).

Yet another preferred embodiment of the present invention is a process as described above, further comprising reacting the cyclopropane derivative of formula (Ib) with a hydroxide donor to produce a compound of formula (III),

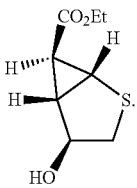
(III)

The following examples are illustrative of the present invention and are not intended to be limiting.

EXAMPLES

Preparation Example 1

Synthesis of Tosyl Azide

A solution of 35 g. (0.5 moles) of sodium azide in 200 ml of water was placed in a 2 litre Erlenmeyer flask and diluted with 400 ml of 90% aqueous ethanol. To this solution was added with stirring a warm (45° C.) solution of 96 g. (0.50 mole) of p-toluenesulfonyl chloride in 1 litre of 99% ethanol. During the addition, sodium chloride separated. The reaction mixture was stirred at room temperature for 2.5 hours. Most of the solvent is removed at 35° C. (15 mm) with a rotary evaporator. The residue was mixed with 1.2 liters of water in a separatory funnel, and the oily p-toluenesulfonyl azide separated. This oil was washed with two 100 ml portions of water and dried over anhydrous sodium sulfate. Filtration with suction gave 50 g (60%, based on p-toluenesulfonyl chloride) of pure, colorless p-toluenesulfonyl azide which completely crystallised on standing at 5°.

Preparation Example 2

Synthesis of Dimethyldiazomalonate 9.9 g. (0.075 mole) of dimethyl malonate, 50 ml of anhydrous acetonitrile, and 7.6 g (0.075 mole) of triethylamine (b.p. 88.5-90.5° C.) were added to a 300 ml double-jacketed flask with a dropping funnel, reflux condenser and mechanical stirrer (Rushton). The temperature of the mixture was adjusted to 20° C., and 14.8 g (0.075 mole) of p-toluenesulfonyl azide in 50 ml of CH$_3$CN is added dropwise with vigorous stirring over 15 minutes. The addition caused the reaction mixture to warm to 38-40° C. and assume a yellow colour. After the mixture had been stirred at room temperature for 2.5 hours, the solvent was evaporated at 35° C. (12 mm). The partially crystalline residue was triturated with 100 ml of ether, and the mixture, including the insoluble residue, was placed in a 500 ml separatory funnel. The mixture was washed successively with a 50 ml solution of potassium hydroxide (2N) and a 50 ml solution of potassium hydroxide (0.5N) solution. The yellow-orange ethereal phase was dried over anhydrous sodium sulfate, and the solvent evaporated at 35° (15 mm) until the residue had attained a constant weight. The yellow-orange diazo ester weighed 5 g. The product was checked by $^1$HNMR spectroscopy and found to be ca. 90% pure.

Preparation Example 3

Synthesis of Ethyldiazoacetate (EDA) in Microreactor

A 10% solution of glycine ester salt, 10% NaNO$_2$ solution and 5% H$_2$SO$_4$ solution were each prepared in cold water. First the glycine ester solution (10%) and thiophene were mixed in a SS316 T-mixer. To this two phase mixture NaNO$_2$ (10%) was mixed in a second T-mixer. To this mixture 5% H$_2$SO$_4$ was mixed in a third T-mixer. The reaction mixture was then allowed to pass through SS316 (stainless steel) tubular microreactor of 1.27 mm internal diameter and volume of 8 ml. The temperature of the microreactor was set to 5° C. using an ice-water bath. All the chemicals were dosed using HPLC pumps. The product was collected in a 5% NaHCO$_3$ solution. The two phase reaction mixture containing water and thiophene was separated and the organic phase was analysed using GC. Mol ratio NaNO$_2$/Glycine ester salt was 1.2. Mol ratio H$_2$SO$_4$/Glycine ester salt was 0.06. Volume ratio thiophene/glycine solution was 3. Residence time was 1 min. Yield was 70%.

Comparative Example 1

Reaction of butyl acrylate and dimethyldiazomalonate was carried out in a batch reactor equipped with a condenser, at a molar ratio of 10. Various conditions were tested and the results are shown below. Analysis was carried out using GC MS and NMR. (DCE=Dichloroethane)

| Rxn no. | Catalyst | Temp. | Solvent | Comments |
|---|---|---|---|---|
| 1 | — | 72-75 C. | DCE | $N_2$ evolution observed. But very slow GC-MS shows definite presence of pyrazoline byproduct. After isolation, quantity of product was much less. |
| 2 | $Rh_2(OAc)_4$ | 80 C. | DCE | $N_2$ evolution fast. Many byproducts observed in GC-MS |
| 3 | Cu metal piece | 90 C. | $CH_3CN$ | Desired cyclopropane reaction product produced. |
| 4 | $Rh_2(OAc)_4$ | 45 C. | DCM | Again many peaks obs. in GC-MS |
| 5 | Cu metal piece | 110 C. | DCE | Desired cyclopropane reaction product produced. No pyrazoline byproduct was seen in this reaction. Around 50% conversion of diazomalonate observed. |

Comparative Example 2

10 mmol of styrene was added to 1 mmol of diethyldiazomalonate (DEDM) in dichloroethane (DCE) at 110° C. A small copper metal piece of copper tubing was cut and added to the reaction mixture. Diethyldiazomalonate was not added dropwise. The desired product was produced in good yield (50%). $^1$HNMR of the product compares with that of a commercial sample supplied by Aldrich. $^1$H-NMR ($CDCl_3$, 300 MHz): δ=0.84 (t, 3H, $CH_3$); 1.30 (t, 3H, $CH_3$); 1.71 (m, 1H), 2.19 (m, 1H), 3.22 (m, 1H); 3.83 (m, 2H, $CH_2$) 4.25 (m, 2H, $CH_2$); 7.26 (m, 5H, Phe).

Example 1

50% styrene solution and 4% DEDM solution in DCE were mixed in the required ratio in a T-mixer. Spring type copper tubing of 1.65 mm internal diameter and volume of 8.6 ml was used as a reactor (acts also as catalyst). The reactor was placed in the oil bath and the temperature was varied between 120-220° C.

| | Reactor | | | |
|---|---|---|---|---|
| No | Temp °C. | Residence time min | Feeds Ratio Styrene/DEDM | Yield % |
| M1 | 160 | 15.0 | 14 | 9.0 |
| M2 | 160 | 10 | 14 | 22.6 |
| M3 | 160 | 5 | 14 | 15.5 |
| M4 | 160 | 2 | 14 | 10.5 |
| M5 | 185 | 15 | 14 | 6.5 |
| M6 | 185 | 10 | 14 | 18.5 |
| M7 | 185 | 5 | 14 | 22.3 |
| M8 | 185 | 2 | 14 | 17.9 |
| M9 | 185 | 5 | 4 | 3.9 |
| M10 | 185 | 2 | 4 | 1.5 |
| M11 | 180 | 5 | 6 | 5.3 |
| M12 | 180 | 10 | 6 | 5.7 |
| M13 | 180 | 5 | 2 | 1.0 |
| M14 | 180 | 2 | 4 | 7.4 |
| M15 | 180 | 5 | 4 | 12.9 |
| M22 | 130 | 3.0 | 3 | 10.0 |
| M23 | 150 | 2.9 | 3 | 7.9 |
| M24 | 170 | 2.9 | 3 | 12.9 |
| M26 | 200 | 2.9 | 3 | 49.6 |
| M27 | 200 | 1.9 | 3 | 55.2 |
| M28 | 200 | 1.4 | 3 | 50.2 |
| M29 | 130 | 10 | 5 | 1.9 |
| M30 | 130 | 5 | 5 | 0.0 |
| M31 | 160 | 10 | 5 | 66.3 |
| M32 | 160 | 5 | 5 | 24.9 |
| M33 | 180 | 10 | 5 | 88.8 |
| M34 | 180 | 5 | 5 | 79.1 |
| M35 | 200 | 3 | 5 | 28.1 |
| M36 | 200 | 5 | 5 | 53.2 |
| M37 | 170 | 10 | 5 | 58.9 |
| M38 | 180 | 3 | 5 | 51.3 |
| M39 | 200 | 2 | 5 | 37.3 |

Comparative Example 3

25% styrene solution and 4% DEDM solution in toluene were mixed together in the required ratio in a stainless steel T-mixer. Spring type stainless steel tubing of 1.27 mm internal diameter and volume of 4.28 ml was used as a reactor. The reactor was placed in an oil bath and the temperature was varied between 160-220 C.

| | Reactor | | | |
|---|---|---|---|---|
| No | Temp °C. | Residence time Min | Feeds Ratio Styrene/DEDM | Yield % |
| S1 | 160 | 5.0 | 5 | 0 |
| S2 | 160 | 10 | 5 | 0 |
| S3 | 180 | 5 | 5 | 11.4 |
| S4 | 180 | 10 | 5 | 18.5 |
| S5 | 200 | 5 | 5 | 19.8 |
| S6 | 200 | 10 | 5 | 12.9 |
| S7 | 200 | 3 | 5 | 18.9 |

The above reactions were repeated using a stainless steel reactor having a volume of 8.5 ml.

| | Reactor | | | |
|---|---|---|---|---|
| No | Temp °C. | Residence time Min | Feeds Ratio Styrene/DEDM | Yield % |
| S8 | 160 | 5 | 5 | 0 |
| S9 | 180 | 5 | 5 | 11.7 |

-continued

| No | Reactor Temp °C | Residence time Min | Feeds Ratio Styrene/DEDM | Yield % |
|---|---|---|---|---|
| S10 | 180 | 10 | 5 | 17.1 |
| S11 | 200 | 10 | 5 | 18.5 |
| S12 | 200 | 5 | 5 | 21.9 |
| S13 | 220 | 5 | 5 | 27.6 |

Example 2

The procedure of Example 1 was repeated, but using toluene as a solvent and the same copper tubing but after a period of non-use of two months.

25% styrene solution and 4% DEDM solution in toluene were mixed together in the required ratio in a T-mixer. Same copper tubing of 1.65 mm internal diameter and volume of 8.6 ml was used as a reactor as described before.

| No | Reactor Temp °C | Residence time Min | Feeds Ratio Styrene/DEDM | yield % |
|---|---|---|---|---|
| M41 | 180 | 5 | 5 | 83.9 |
| M42 | 180 | 3 | 5 | 75.0 |
| M43 | 180 | 3 | 3 | 60.8 |
| M44 | 180 | 3 | 1 | 64.8 |
| M45 | 200 | 3 | 5 | 70.0 |
| M46 | 200 | 5 | 5 | 64.3 |
| M47 | 200 | 3 | 3 | 54.2 |
| M48 | 200 | 3 | 1 | 55.1 |

From the results it seems that copper tubing after using several times still performs the same way as before.

Example 3

The procedure of Example 1 was repeated, but using toluene as a solvent. During the reaction diazomalonate decomposes and produces $N_2$ gas, which occupies a certain volume of the reactor. Accordingly the actual residence time (RT) will be lower than that measured. From the concentration of the DEDM and pressure and temperature of the reaction the actual residence time was calculated using the ideal gas law (PV=nRT).

| RT = 5 and 10 min (calculated RT = 4.2 min and RT = 8.5 min) | | | |
|---|---|---|---|
| Temp. | Ratio Styrene/DEDM | RT = 5 yield | RT = 10 yield |
| 130 | 5 | 0.0 | 2 |
| 160 | 5 | 25.0 | 66 |
| 180 | 5 | 84.0 | 88 |
| 200 | 5 | 64.0 | — |

Example 4

The procedure of Example 1 was repeated, but using toluene as a solvent. The actual residence time was calculated as in Example 3.

| Temp. | RT | Ratio Styrene/DEDM | T = 180 C. yield | T = 200 C. yield | RT calculated |
|---|---|---|---|---|---|
| 180 | 10 | 5 | 88.0 | — | 8.4 |
| 180 | 5 | 5 | 85.0 | 64 | 4.2 |
| 180 | 3 | 5 | 70.0 | 54 | 2.5 |

Example 5

The procedure of Example 1 was repeated, but using toluene as a solvent. The actual residence time was calculated as in Example 3.

| Temp. | RT | Ratio Styrene/DEDM | T = 180 C. yield | T = 200 C. yield |
|---|---|---|---|---|
| 180 | 3 | 5 | 75.0 | 70 |
| 180 | 3 | 3 | 60.0 | 54 |
| 180 | 3 | 1 | 58.0 | 55 |

Example 6

A solution of ethyldiazoacetate (EDA; 1 wt %) in thiophene was prepared. The solution was well mixed by stirring for a while or by shaking. The solution was then pumped using HPLC pumps through a spring-type copper tubing of 1.65 mm internal diameter having a 4 ml volume placed in an oil bath at certain temperature. The residence time of the reaction was controlled by adjusting the flow rate. After the reaction mixture passed through the reactor, it passed through stainless steel tubing for cooling. A pressure control device was used to maintain a pressure of 25 bars in the reactor. Samples were collected in a glass bottle and analyzed by GC.

| Temp °C. | Residence time Min | dimers/% | cyclopropyl yield % |
|---|---|---|---|
| 140 | 4 | 7.4 | 19.2 |
| 150 | 4 | 7.5 | 23.3 |
| 150 | 4 | 8.2 | 24.5 |
| 160 | 4 | 8.6 | 26.9 |
| 160 | 3 | 7.8 | 25.6 |
| 160 | 2 | 7.0 | 25.6 |
| 170 | 2 | 6.5 | 24.3 |
| 170 | 1 | 6.7 | 25.2 |
| 180 | 1 | 7.0 | 26.4 |
| 180 | 2 | 6.2 | 24.6 |
| 200 | 0.8 | 9.0 | 18.2 |
| 200 | 1.0 | 10.9 | 19.8 |
| 200 | 1.0 | 11.1 | 18.2 |

Example 7

The procedure of Example 1 was repeated, but using copper tubing of volume 8.5 ml.

| Temp °C. | Residence time Min | EDA conversion % | dimers/% | cyclopropyl yield % |
|---|---|---|---|---|
| 110 | 11 | 84.2 | 4.2 | 20 |
| 100 | 17 | 86.8 | 8.9 | 19 |
| 100 | 11 | 82.9 | 10.3 | 19 |
| 100 | 9 | 81.3 | 10.9 | 20 |
| 100 | 7 | 77.5 | 11.8 | 21 |
| 130 | 9 | 92.8 | 11.4 | 24 |
| 80 | 2 | 9.8 | 0.0 | 2 |
| 80 | 4 | 41.3 | 5.8 | 9 |
| 80 | 9 | 62.7 | 8.1 | 13 |
| 80 | 11 | 68.6 | 8.8 | 15 |
| 110 | 4 | 75.0 | 8.7 | 18 |
| 110 | 9 | 89.7 | 10.0 | 22 |

Comparative Example 4

The following catalysts were added to 3 ml of thiophene in a round bottomed flask placed in an oil bath at the following temperatures. A solution of 1 mmol of EDA in 2 ml of thiophene was added drop-wise over 1 hour to the flask containing the catalyst, whilst stirring (see table below). A sample was then taken and analyzed by GC.

| Catalyst | Cat. mol % | Time H | temp. C. | EDA conv. % | cyclopropyl % |
|---|---|---|---|---|---|
| Rh(OAc)$_2$ | 0.5 | 3 | 45 | 100 | 59 |
| Ru(II)complex | 1 | 5 | 80 | 65 | 11 |
| Cu metal | | 6 | 80 | 46 | 7 |

Example 8

A solution of ethyldiazoacetate (EDA) in thiophene was prepared. The solution was well mixed by stirring for a while or by shaking. The solution was then pumped using HPLC pumps through a packed tube reactor having an internal diameter of 2.1 mm and a length of 25 cm, and containing copper particles having an average diameter of 250 μm. The packed tube reactor was placed in an oil bath at a certain temperature. The residence time of the reaction was controlled by adjusting the flow rate. After the reaction mixture passed through the reactor, it was passed through stainless steel tubing for cooling. A pressure control device was used to maintain a pressure of 25 bars in the reactor. Samples were collected in a glass bottle and analyzed by gas chromatography.
0.5 wt % EDA solution used:

| Temp °C. | res time sec | EDA ml/min | EDA conversion % | dimers % | cyclopropyl yield % |
|---|---|---|---|---|---|
| 185 | 10.2 | 5 | 97.5 | 4.05 | 29.56 |
| 185 | 13.2 | 4 | 99.7 | 3.29 | 29.80 |
| 185 | 17.4 | 3 | 100.0 | 3.30 | 29.11 |
| 185 | 25.8 | 2 | 100.0 | 3.28 | 28.97 |
| 185 | 30 | 1.72 | 100.0 | 3.29 | 28.78 |
| 185 | 60 | 0.866 | 100.0 | 3.19 | 29.72 |

2 wt % EDA solution used:

| Temp °C. | res time Sec | EDA ml/min | EDA conversion % | dimers % | cyclopropyl yield % |
|---|---|---|---|---|---|
| 185 | 17.32 | 3 | 98.87 | 15.62 | 27.17 |
| 185 | 5.20 | 10 | 93.81 | 15.53 | 28.68 |
| 185 | 6.50 | 8 | 96.03 | 15.06 | 27.64 |
| 185 | 8.66 | 6 | 98.59 | 15.16 | 27.62 |

Example 9

The method of Example 8 was repeated using a solution of 5 wt % EDA and a mixture of 3.5 wt % copper particles having an average diameter of 150 μm with Al$_2$O$_3$ (an inert material) with an average diameter of 300 μm.

| Temp °C. | res time min | EDA ml/min | EDA conversion % | dimers % | cyclopropyl yield % |
|---|---|---|---|---|---|
| 160 | 1.00 | 0.866 | 100 | 1.9 | 20.8 |
| 160 | 0.67 | 1.29 | 98 | 2.1 | 28.9 |
| 160 | 0.50 | 1.72 | 93 | 2.1 | 27.0 |
| 175 | 1.00 | 0.866 | 100 | 3.6 | 16.5 |
| 175 | 0.67 | 1.29 | 100 | 2.2 | 29.7 |
| 175 | 0.30 | 2.88 | 97 | 2.2 | 31.5 |
| 175 | 0.26 | 3.31 | 96 | 2.1 | 30.9 |
| 180 | 0.20 | 4.33 | 94 | 2.1 | 30.8 |
| 180 | 0.50 | 1.72 | 100 | 2.2 | 30.7 |
| 180 | 0.40 | 2.165 | 100 | 2.2 | 31.9 |

Example 10

The method of Example 8 was repeated using a solution of 2 wt % EDA and a mixture of 3.5 wt % CuO particles having a diameter of from 50 to 150 μm with Al$_2$O$_3$ (an inert material) with an average diameter of 300 μm.

| Temp °C. | res time Sec | EDA conversion % | dimers % | cyclopropyl yield % |
|---|---|---|---|---|
| 190 | 1.66 | 80.13 | 9.35 | 17.82 |
| 190 | 2.08 | 83.00 | 9.98 | 18.85 |
| 190 | 2.77 | 90.68 | 10.19 | 20.74 |
| 190 | 4.16 | 97.13 | 10.27 | 22.39 |
| 190 | 8.31 | 99.68 | 10.26 | 22.35 |

Comparative Example 5

The method of Example 9 was repeated, but in the absence of copper particles. The desired cyclopropyl product was not produced; only dimers were observed.

The invention claimed is:

1. A process for the preparation of a cyclopropane derivative of Formula (I),

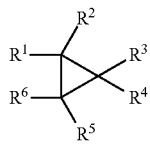

by reacting an olefin of Formula (II),

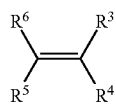

with a carbene of the formula:$CR^1R^2$, in a reaction vessel, optionally in the presence of a solvent, wherein, $R^1$ and $R^2$ are each independently hydrogen, $C_1$-$C_6$ alkyl, $C_2$-$C_6$ alkenyl, aryl, heteroaryl, heterocyclyl, carbocyclyl, heterocyclyl, —C(O)$R^7$ or —N$R^8{}_2$;

$R^3$, $R^4$, $R^5$ and $R^6$ are each independently hydrogen, $C_1$-$C_6$ alkyl, $C_1$-$C_6$ alkoxy, $C_2$-$C_6$ alkenyl, aryl, aryloxy, heteroaryl, heterocyclyl, carbocyclyl, heterocyclyl, —C(O)$R^9$, —N$R^{10}{}_2$, —S$R^{11}$, —S(O)$R^{11}$, or —SO$_2R^{11}$, or $R^3$ and $R^6$ are as defined above and $R^4$ and $R^5$ together form a ring, which ring is carbocyclyl, heterocyclyl, aromatic or heteroaromatic;

$R^7$ is hydrogen, hydroxy, $C_1$-$C_6$ alkyl, $C_1$-$C_6$ alkoxy, aryl, aryloxy, heteroaryl or —N$R^{10}{}_2$;

$R^8$ is hydrogen, $C_1$-$C_6$ alkyl, $C_1$-$C_6$ alkenyl, aryl, heteroaryl, carbocyclyl or heterocyclyl;

$R^9$ is hydrogen, hydroxy, $C_1$-$C_6$ alkyl, $C_1$-$C_6$ alkoxy, aryl, aryloxy or heteroaryl;

$R^{10}$ is hydrogen, $C_1$-$C_6$ alkyl, $C_2$-$C_6$ alkenyl, aryl, heteroaryl, carbocyclyl, heterocyclyl or C(O)$R^{12}$;

$R^{11}$ is hydrogen, $C_1$-$C_6$ alkyl, $C_2$-$C_6$ alkenyl, aryl, heteroaryl, carbocyclyl or heterocyclyl; and $R^{12}$ is hydrogen, hydroxy, $C_1$-$C_6$ alkyl, $C_1$-$C_6$ alkoxy, aryl, or aryloxy, in the presence of copper metal or copper oxide, wherein the process is a continuous process.

2. A process according to claim 1, wherein a portion of an inner surface of the reaction vessel is copper metal.

3. A process according to claim 1 wherein the reaction vessel is a microreactor.

4. A process according to claim 1, wherein a solvent is present and said solvent is recycled.

5. A process according to claim 1, wherein no solvent is present.

6. A process according to claim 1, wherein unreacted olefin of Formula (II) is recycled.

7. A process according to claim 1, comprising generating the carbene in situ from a diazo compound of the formula $N_2CR^1R^2$, wherein $R^1$ and $R^2$ are as defined in claim 1.

8. A process according to claim 7, further comprising the step of producing the diazo compound of the formula $N_2CR^1R^2$, in a continuous process, and continuously with the preparation of the cyclopropane derivative of Formula (I).

9. A process according to claim 8, wherein the diazo compound of the formula $N_2CR^1R^2$ is produced in a process utilizing at least one microreactor.

10. A process according to claim 1, wherein the cyclopropane derivative of Formula (I) is a cyclopropane derivative of Formula (I'),

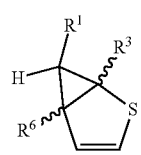

wherein $R^1$, $R^3$ and $R^6$ are as defined in claim 1.

11. A process according to claim 1, wherein the cyclopropane derivative of Formula (I) is a cyclopropane derivative of Formula (Ia),

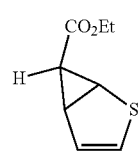

the olefin of Formula (II) is thiophene, the carbene of formula:$CR^1R^2$ is ethoxycarbonyl carbene (:CHCO$_2$Et) and the diazo compound of formula $N_2CR^1R^2$ is ethyldiazoacetate ($N_2$CHCO$_2$Et).

12. A process according to claim 1, further comprising the step of isolating a cyclopropane derivative of (Ib),

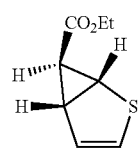

from the cyclopropane derivative of Formula (Ia).

13. A process for the preparation of a cyclopropane derivative of Formula (Ia),

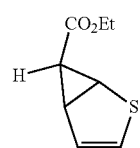

by reaction of thiophene with:CHCO$_2$Et, generated in situ from ethyldiazoacetate ($N_2$CHCO$_2$Et), in a copper metal microreactor, wherein the thiophene is recycled; the ethyldiazoacetate is produced in a continuous process, utilizing at least one microreactor, and continuously with the preparation of the cyclopropane derivative of Formula (Ia).

14. A process according to claim 13, further comprising the step of isolating a cyclopropane derivative of (Ib),
(Ib)
from the cyclopropane derivative of Formula (Ia).
15. A process according to claim 12, further comprising reacting the cyclopropane derivative of formula (Ib) with a hydroxide donor to produce a compound of formula (III),
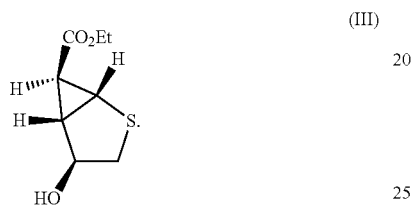
(III)
* * * * *